United States Patent
Hiura et al.

(10) Patent No.: US 9,533,940 B2
(45) Date of Patent: Jan. 3, 2017

(54) METHOD FOR PRESERVING 1,5-PENTANEDIAMINE OR SALT THEREOF, METHOD FOR PREVENTING DISCOLORATION OF 1,5-PENTANEDIAMINE OR SALT THEREOF, AND 1,5-PENTANEDIAMINE OR SALT THEREOF IN CONTAINER

(71) Applicant: AJINOMOTO CO., INC., Tokyo (JP)

(72) Inventors: Takehiro Hiura, Kanagawa (JP); Masataka Yamamoto, Kanagawa (JP); Yasuhiro Maruta, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/820,108

(22) Filed: Aug. 6, 2015

(65) Prior Publication Data
US 2015/0344405 A1    Dec. 3, 2015

Related U.S. Application Data

(63) Continuation of application No. PCT/JP2014/052934, filed on Feb. 7, 2014.

(30) Foreign Application Priority Data

Feb. 8, 2013  (JP) .................................. 2013-023851

(51) Int. Cl.
*C07C 209/90* (2006.01)

(52) U.S. Cl.
CPC .................................. *C07C 209/90* (2013.01)

(58) Field of Classification Search
CPC .................................................. C07C 209/90
See application file for complete search history.

(56) References Cited

U.S. PATENT DOCUMENTS

| 5,449,832 | A |   | 9/1995  | Van Court Carr et al. |
| 5,714,634 | A | * | 2/1998  | Casale ................... C07C 209/90 203/12 |
| 2006/0281951 | A1 | * | 12/2006 | Lee ....................... C07C 209/84 564/511 |
| 2010/0274057 | A1 |   | 10/2010 | Peters et al. |
| 2013/0071888 | A1 |   | 3/2013  | Sawai et al. |

FOREIGN PATENT DOCUMENTS

| CN | 102056889 A | 5/2011 |
| CN | 102844440 A | 12/2012 |
| JP | 8-119910    | 5/1996 |
| JP | 2008-174476 | 7/2008 |
| JP | 2008-189661 | 8/2008 |
| JP | 2009-523144 | 6/2009 |
| JP | 2009-155284 | 7/2009 |
| JP | 2012-106935 | 6/2012 |
| JP | 2006-182666 | 7/2013 |

OTHER PUBLICATIONS

International Search Report for PCT Patent App. No. PCT/JP2014/052934 (Apr. 1, 2014).
Office Action for Chinese Patent App. No. 201480007896.4 (Mar. 17, 2016) with English language translation thereof.

* cited by examiner

*Primary Examiner* — Shailendra Kumar
(74) *Attorney, Agent, or Firm* — Shelly Guest Cermak; Cermak Nakajima & McGowan LLP

(57) ABSTRACT

Means of preserving 1,5-pentanediamine or a salt thereof without deterioration is provided. 1,5-pentanediamine or a salt thereof is preserved by adjusting any of a water content of 1,5-pentanediamine or a salt thereof purified through a distillation process, a temperature condition, and a material that comes into contact with 1,5-pentanediamine or a salt thereof.

8 Claims, No Drawings

METHOD FOR PRESERVING 1,5-PENTANEDIAMINE OR SALT THEREOF, METHOD FOR PREVENTING DISCOLORATION OF 1,5-PENTANEDIAMINE OR SALT THEREOF, AND 1,5-PENTANEDIAMINE OR SALT THEREOF IN CONTAINER

This application is a Continuation of, and claims priority under 35 U.S.C. §120 to, International Application No. PCT/JP2014/052934, filed Feb. 7, 2014, and claims priority therethrough under 35 U.S.C. §119 to Japanese Patent Application No. 2013-023851, filed Feb. 8, 2013, the entireties of which are incorporated by reference herein.

BACKGROUND OF THE INVENTION

Field of the Invention

The present invention relates to a method for preserving 1,5-pentanediamine or a salt thereof, a method for preventing discoloration of 1,5-pentanediamine or a salt thereof, and 1,5-pentanediamine or a salt thereof in a container. In the description, 1,5-pentanediamine is hereinafter written as "1,5-PD."

Brief Description of the Related Art 1,5-PD is a substance that is predicted to be in a demand as a resin raw material such as a polyamide resin or a pharmaceutical intermediate. Since 1,5-PD can be produced from a non-petroleum-based raw material, 1,5-PD industrially has attracted attention for its potential usefulness for reduction in environmental impact.

1,5-PD can be produced by dry-distilling lysine or decarboxylating lysine using an enzyme. In view of the demand, research and development of a method for producing 1,5-PD or a salt thereof in an industrial scale have intensively proceeded, but knowledge about a preservation method after production has been elusive. A preservation method in which the pH of a solution containing 1,5-PD and the like is adjusted to a predetermined range has been disclosed (Patent Literature 1: Japanese Patent Application Laid-Open No. 2008-174476).

SUMMARY OF THE INVENTION 1,5-PD or a salt thereof is a substance that is often used as an intermediate raw material in industrial production as described above. In the manufacturing industry at a site where 1,5-PD or a salt thereof is used as a raw material, 1,5-PD or a salt thereof cannot be necessarily used immediately after production thereof. A manufacturer of 1,5-PD or a salt thereof and a manufacturer who produces a product from 1,5-PD or a salt thereof may be separate entities. In terms of production site, a production site of 1,5-PD or a salt and a production site of the product produced from 1,5-PD or a salt thereof are in different locations in many cases. For this reason, 1,5-PD or a salt thereof may be used several days or several weeks after production thereof, which includes a transport period or the like. Therefore, it is important to preserve 1,5-PD or a salt thereof on an industrial production scale without deterioration. In particular, since 1,5-PD or a salt thereof is likely to discolor, development of a preservation method in which discoloration is prevented has been urgently required.

In view of such circumstances, the aspect of the present invention is to provide means of preservation of 1,5-PD or a salt thereof for a predetermined period of time without deterioration. The specific aspect of the present invention is to provide means capable of preservation of 1,5-PD or a salt thereof without discoloration for a predetermined period of time.

A preservation method is described for purified 1,5-PD or a salt thereof that is affected by a water content thereof, a temperature condition, a material quality of a container for preservation, and the like as important factors.

It is an aspect of the present invention to provide a method for preserving purified 1,5-pentanediamine or a salt thereof which has a water content, the method comprising adjusting said water content in the purified 1,5-pentanediamine or a salt thereof to more than 1% by weight and not more than 50% by weight.

It is a further aspect of the present invention to provide the method as described above, wherein said adjusting comprises adding water to the purified 1,5-pentanediamine or a salt thereof.

It is a further aspect of the present invention to provide the method as described above, wherein said adjusting comprises adding water so that said water content is 3% by weight or more and not more than 8% by weight; wherein said purified 1,5-pentanediamine or a salt thereof has a purity of 98% by weight or more.

It is a further aspect of the present invention to provide the method as described above, wherein said adjusting is performed at a temperature of 40° C. or lower.

It is a further aspect of the present invention to provide the method as described above, wherein said purified 1,5-pentanediamine or a salt thereof is not in contact with iron, a low density polyethylene, silicon, a rubber, and polyvinylidene chloride.

It is a further aspect of the present invention to provide the method as described above, wherein said adjusting is conducted in a container which includes an inner face that is in contact with said purified 1,5-pentanediamine or a salt thereof, and is coated with glass, polypropylene, a high density polyethylene, a stainless steel, or polytetrafluoroethylene.

It is a further aspect of the present invention to provide a method for preventing discoloration of purified 1,5-pentanediamine or a salt thereof which has a water content, the method comprising adjusting said water content in the purified 1,5-pentanediamine or a salt thereof to more than 1% by weight and not more than 50% by weight.

It is a further aspect of the present invention to provide a packaged 1,5-pentanediamine or salt thereof, comprising a container for preservation of 1,5-pentanediamine or a salt thereof, and purified 1,5-pentanediamine or a salt thereof contained in the container, wherein the container includes an inner face in contact with the purified 1,5-pentanediamine or a salt thereof, said inner face is coated with glass, polypropylene, a high density polyethylene, a stainless steel, or polytetrafluoroethylene, and, wherein iron, a low density polypropylene, silicon, a rubber, and polyvinylidene chloride are not exposed on the inner face, wherein a water content in the 1,5-pentanediamine or a salt thereof is more than 1% by weight and not more than 50% by weight.

According to the present invention, 1,5-PD or a salt thereof can be preserved while discoloration is suppressed for a predetermined period of time.

DETAILED DESCRIPTION OF THE EXEMPLARY EMBODIMENTS

<1. Method for Preserving 1,5-PD or a Salt Thereof>

The present invention provides a method for preserving 1,5-PD or a salt thereof. 1,5-PD or a salt thereof can be controlled by the water content of 1,5-PD or a salt thereof, a temperature condition, and/or a material that comes into contact with 1,5-PD or a salt thereof.

1,5-PD or a salt thereof can be preserved as described herein. At least one of 1,5-PD, and/or a salt thereof can be preserved, and may be preserved during mixing of these.

1,5-PD (1,5-pentadiamine, chemical formula: $H_2N(CH_2)_5NH_2$) is a compound that can also be referred to by its common name "cadaverine". 1,5-PD is a strong base, and is colorless and transparent in a liquid state.

The term "salt of 1,5-PD" represents a salt formed from 1,5-PD and an acid. The type of salt of 1,5-PD is not particularly limited. The salt of 1,5-PD may be a monovalent salt or a divalent salt. The type of acid forming a salt with 1,5-PD may be an inorganic acid or an organic acid, and be a monovalent acid or divalent or higher valency acid. Examples of the acid may include hydrochloric acid, sulfuric acid, nitric acid, carbonic acid, carboxylic acid, phosphoric acid, sulfonic acid, and the like. Examples of carboxylic acid may include formic acid, acetic acid, adipic acid, glutaric acid, succinic acid, sebacic acid, and the like.

1,5-PD or a salt thereof can be generally produced by dry-distilling lysine. or decarboxylating lysine by action of an enzyme, and produced 1,5-PD can be further purified.

The preservation method can be suitable as a method for preserving purified 1,5-PD or a salt thereof. In the preservation method, a purification method of "purified 1,5-PD or a salt thereof" that is the subject for preservation is not particularly limited. Examples thereof may include distillation, crystallization, and the like. Specifically, purified 1,5-PD or a salt thereof may be 1,5-PD or a salt thereof that has been purified by a distillation process or a crystallization process. Examples of distillation method may include general distillation methods such as a multi-step distillation method.

The purity (W/W) of 1,5-PD or a salt thereof after purification is 90% by weight or more, 95% by weight or more, 96% by weight or more, 97% by weight or more, 98% by weight or more, 99% by weight or more, 99.5% by weight or more, 99.8% by weight or more, and 100% by weight.

The purity (concentration) of 1,5-PD or a salt thereof can be measured by a usual analysis. Examples of the analysis may include gas chromatography, liquid chromatography, and the like.

In the preservation method, the water content of 1,5-PD or a salt thereof is adjusted to a predetermined content. When the water content is adjusted to a predetermined range, discoloration of 1,5-PD or a salt thereof can be suppressed.

The lower limit of water content of 1,5-PD or a salt thereof to be provided may include, for example, more than 1% by weight (not including 1% by weight), 2% by weight or more, 3% by weight or more, 4% by weight or more, and 5% by weight or more.

The upper limit of water content of 1,5-PD or a salt thereof to be provided may include, for example, 50% by weight or less, 40% by weight or less, 30% by weight or less, 20% by weight or less, 15% by weight or less, 14% by weight or less, 13% by weight or less, 12% by weight or less, 11% by weight or less, 10% by weight or less, 9% by weight or less, 8% by weight or less, 7% by weight or less, and 6% by weight or less.

When the temperature is higher than a normal temperature (20° C.±15° C., that is, 5° C. to 35° C.), for example, higher than 40° C. or higher than 50° C., it is preferable that the water content be low. Therefore, when the temperature is higher than 40° C. or higher than 50° C., it is suitable that the upper limit of the water content be specifically 20% by weight or less, 15% by weight or less, 14% by weight or less, 13% by weight or less, 12% by weight or less, 11% by weight or less, 10% by weight or less, 9% by weight or less, 8% by weight or less, 7% by weight or less, or 6% by weight or less.

When 1,5-PD or a salt thereof is purified by a process such as distillation, 1,5-PD or a salt thereof is likely to be purified to a state where the purity is extremely high as described above. 1,5-PD or a salt thereof that is purified by the process such as distillation is preserved after the water content of 1,5-PD or a salt thereof is adjusted to 1% by weight or more and 20% by weight or less by adding water to the 1,5-PD or a salt thereof. In this case, the upper limit of water content of 1,5-PD or a salt thereof is the same as the water content described above except for 20% by weight or less. In contrast, the lower limit thereof is the same as the lower limit of water content described above.

When 1,5-PD or a salt thereof is preserved, it can be preserved under a predetermined temperature. Particularly, the upper limit of temperature can be provided. The upper limit of the temperature may include 40° C. or lower, 30° C. or lower, 25° C. or lower, 24° C. or lower, 23° C. or lower, 22° C. or lower, 21° C. or lower, 20° C. or lower, 19° C. or lower, 18° C. or lower, 17° C. or lower, 16° C. or lower, 15° C. or lower, and 10° C. or lower. The lower limit of the temperature is as described in the following Examples. 1,5-PD or a salt thereof can be well preserved in a liquid state even at −20° C. For ease of handling or the like, the lower limit of temperature can be generally, for example, 0° C. or higher or 5° C. or higher.

The mechanism of action for suppressing discoloration is not necessarily clear. However, it is assumed that 1,5-PD or a salt thereof can be stabilized without deterioration to suppress discoloration by adjusting the water content of 1,5-PD or a salt thereof and the temperature condition to the predetermined ranges as described above.

In the method for preserving 1,5-PD or a salt thereof, 1,5-PD or a salt thereof should not be in contact with iron (Fe), a low density polyethylene, silicon, a rubber, and polyvinylidene chloride. Since these substances may be eroded by 1,5-PD or a salt thereof, these substances are assumed to facilitate the discoloration of 1,5-PD or a salt thereof, but this is not necessarily clear. Therefore, it is suitable that a container for preservation of 1,5-PD or a salt thereof be a container having such a structure that these materials are not in contact with 1,5-PD or a salt thereof.

1,5-PD or a salt thereof can be kept in a container which includes an inner face that is in contact with 1,5-PD or a salt thereof, and is coated with glass, polypropylene, a high density polyethylene, a stainless steel, or polytetrafluoroethylene. The entire container may be formed from any of these materials, or at least a portion of the container in contact with 1,5-PD or a salt thereof may be formed from any of these material. For example, even when the materials are used in the outer packing of the container which should not be in contact with 1,5-PD, as described above, the container may include a portion in contact with 1,5-PD or a salt thereof, such as an interior and inlet and outlet ports, that is coated with glass, polypropylene, a high density polyethylene, a stainless steel, or polytetrafluoroethylene.

A low density polyethylene (LDPE) is generally distinguished from a high density polyethylene (HDPE) by production method and density. The low density polyethylene is usually produced by a high pressure method. The density of the low density polyethylene is about 0.910 or more and about 0.940 or less. The high density polyethylene is usually produced by a moderate pressure method or a low pressure method. The density of the high density polyethylene is about 0.941 or more.

A stainless steel can be generally classified into five types: martensitic stainless steel, ferritic stainless steel, austenitic stainless steel, dual-phase stainless steel, and precipitation-hardened stainless steel, and any of these can be used. Particular examples include austenitic stainless steel, and more specifically SUS304 or SUS316L.

As polytetrafluoroethylene, a commercially available product such as TEFLON (DuPont) can be used.

1,5-PD or a salt thereof can be preserved in such a condition that 1,5-PD or a salt thereof is not in contact with a gas phase. For example, when 1,5-PD or a salt thereof is preserved in a container, all gases can be evacuated from the container. When 1,5-PD or a salt thereof is in contact with a gas phase, the contact area of the 1,5-PD or a salt thereof with the gas phase should be made as small as possible. Furthermore, when 1,5-PD or a salt thereof is in contact with a gas phase, the amount of water vapor contained in the gas phase should be low.

As described above, the water content, the temperature, and the type of material to be in contact therewith may be each separately applied, or a combination thereof may be applied as appropriate. For example, water is added to 1,5-PD or a salt thereof that has been purified to a purity of 98% by weight or more, 99% by weight or more, or 99.5% by weight or more by distillation. The water is added to adjust the water content in the 1,5-PD or a salt thereof to 3% by weight to 8% by weight or 4% by weight to 6% by weight, and the resultant 1,5-PD or a salt thereof is placed in a sealable tank with an interior that is coated with polypropylene, a high density polyethylene, a stainless steel, or polytetrafluoroethylene, and is preserved at a temperature of 15° C. to 25° C.

In the preservation method, adjustment of pH is optional. According to the preservation method, 1,5-PD or a salt thereof can be well preserved for a predetermined period of time without adjusting the pH by addition of an acid or the like. Therefore, the preservation method is suitable as a method for preserving the form of 1,5-PD.

The preservation time according to the preservation method is optional. The preservation time may be, for example, 1 day or more, 2 days or more, 3 days or more, 4 days or more, 5 days or more, 7 days or more, 10 days or more, 15 days or more, 20 days or more, 30 days or more, 40 days or more, 50 days or more, 60 days or more, 70 days or more, 80 days or more, 90 days or more, 100 days or more, 110 days or more, or 120 days or more.

The preservation time may be, for example, 1 year (365 days) or less, 200 days or less, 180 days or less, 170 days or less, 160 days or less, or 150 days or less.

According to the preservation method, 1,5-PD or a salt thereof can be preserved while discoloration is suppressed by a simple technique for a predetermined period of time. The preservation method is an inexpensive method, and is industrially advantageous.

In the preservation method, 1,5-PD or a salt thereof can be preserved while high purity is maintained. Therefore, even when using a strong base, discoloration can be suppressed. Since it is not necessary that the volume amount be increased by addition of a solvent, this method is excellent in industrial practicality from the viewpoint of transport and preservation space of 1,5-PD or a salt thereof.

<2. Method for Preventing Discoloration of 1,5-PD or a Salt Thereof of the Present Invention>

According to the preservation method, 1,5-PD or a salt thereof can be preserved while discoloration thereof is suppressed. As one aspect, the present invention also provides a method for preventing discoloration of 1,5-PD or a salt thereof.

The method for preventing discoloration is not limited to an aspect of preservation using a container. For example, when the method for preventing discoloration is applied, discoloration of 1,5-PD or a salt thereof during transport via a pipeline or the like can be prevented. In this case, it is suitable that an inner circumferential surface of the pipeline via which 1,5-PD or a salt thereof is transported be coated with the preferred material described above.

<3. A Packaged 1,5-PD or Salt Thereof of the Present Invention>

As another aspect, the present invention further provides a packaged 1,5-PD or salt thereof to which the preservation method of the present invention may apply. One example includes a container for preservation of 1,5-PD or a salt thereof and purified 1,5-PD or a salt thereof contained in this container. The inner face of the container to be in contact with 1,5-PD or a salt thereof are coated with glass, polypropylene, a high density polyethylene, a stainless steel, or polytetrafluoroethylene. And iron, a low density polypropylene, silicon, a rubber, and polyvinylidene chloride are not exposed on the inner face. Furthermore, the water content in the 1,5-PD or a salt thereof is more than 1% by weight and not more than 20% by weight.

Even when such a packaged 1,5-PD or salt thereof is preserved for a predetermined period of time, deterioration such as discoloration is unlikely to occur. Suitable conditions of the water content of 1,5-PD or a salt thereof and the material quality of portion of the container in contact with 1,5-PD or a salt thereof are the same as described in the preservation method of the present invention. It is preferable that a packaged 1,5-PD or salt thereof be at a suitable temperature shown in the preservation method of the present invention.

Examples

Hereinafter, the present invention will be described in more detail with reference to Examples. However, the present invention is not limited to the following Examples.

<1> Preparation of 100% by Weight 1,5-PD Solution

15% by weight 1,5-PD solution was prepared by an enzymatic reaction of a basic solution containing lysine. The resultant 15% by weight 1,5-PD solution was sterilized, decolorized, and then distilled, to prepare 100% by weight 1,5-PD liquid.

The APHA value (color of Hazen unit) of the resultant 100% by weight 1,5-PD solution is 3.

The APHA value was measured with OME 2000 (light path length: 33 nm, CV=3% or less) manufactured by NIPPON DENSHOKU INDUSTRIES CO., LTD. (the APHA value described below was measured similarly).

<2> Evaluation Test of Preservation Method Depending on Difference in Water Content An evaluation test on influence of the water content on preservation stability of 1,5-PD was performed by the following method.

Ultrapure water was added to 100% by weight 1,5-PD solution (water addition amount: 0) prepared in the above <1>, to prepare 1,5-PD solutions in which the water addition amount was 50% by weight, 20% by weight, 10% by weight, or 5% by weight, respectively.

The 1,5-PD liquid of each concentration was placed in a glass flask, the glass flask was placed in a water bath adjusted to 20° C., and the 1,5-PD solution was preserved with stirring for a predetermined period of time.

The APHA value of each liquid was measured every the predetermined period of time. The results of measurement of the APHA values are shown in Table 1.

TABLE 1

TABLE 1: VARIATION OF APHA VALUE DEPENDING ON WATER ADDITION AMOUNT

| ELAPSED | WATER ADDITION AMOUNT (RATIO BY WEIGHT) | | | | |
|---|---|---|---|---|---|
| DAYS | 0% | 5% | 10% | 20% | 50% |
| 0 | 6 | 2 | 5 | 13 | 5 |
| 2 | 16 | 6 | 7 | 8 | 3 |
| 12 | 26 | 3 | 9 | 7 | 3 |
| 18 | 26 | 3 | 8 | 4 | 3 |
| 25 | 25 | 3 | 6 | 5 | 4 |

Each 1,5-PD liquid of which the water addition amount was 0% by weight, 5% by weight, 10% by weight, or 50% by weight was subjected to a preservation test in the same manner as described above. The results of measurement of the APHA values after 143 days are shown in Table 2.

TABLE 2

TABLE 2: VARIATION OF APHA VALUE DEPENDING ON WATER ADDITION AMOUNT

| ELAPSED | WATER ADDITION AMOUNT (RATIO BY WEIGHT) | | | |
|---|---|---|---|---|
| DAYS | 0% | 5% | 10% | 50% |
| 143 | 12 | 5 | 6 | 3 |

As shown in Tables 1 and 2, it was confirmed that the development of coloration could be markedly suppressed by adding water to 1,5-PD.

<3> Evaluation Test of Preservation Method Depending on Difference in Temperature Condition An evaluation test on influence of the temperature on preservation stability of 1,5-PD was performed by the following method.

The 100% by weight 1,5-PD liquid prepared in the above <1> (that is, water addition amount: 0% by weight) and a 1,5-PD solution having a water addition amount of 50% by weight obtained by adding ultrapure water to the 100% by weight 1,5-PD liquid were prepared.

Each 1,5-PD liquid was placed in a glass flask, the temperature of the glass flask was adjusted to −20° C., 5° C., 20° C., 40° C., and 60° C., and the 1,5-PD solution was preserved with stirring for a predetermined period of time.

In a test under a condition of −20° C., the glass flask was placed in a freezer. In tests under other conditions, the glass flask was placed in a water bath.

The APHA value of each liquid was measured at each predetermined time. The results of measurement of the APHA values are shown in Table 3 (in a case of a water addition amount of 0% by weight) and Table 4 (in a case of a water addition amount of 50% by weight).

TABLE 3

TABLE 3: VARIATION OF APHA VALUE DEPENDING ON TEMPERATURE (WATER ADDITION AMOUNT: 0% BY WEIGHT)

| ELAPSED | PRESERVATION TEMPERATURE | | | | |
|---|---|---|---|---|---|
| DAYS | −20° C. | 5° C. | 20° C. | 40° C. | 60° C. |
| 0 | 6 | 6 | 6 | 6 | 6 |
| 2 | 8 | 10 | 16 | 26 | 21 |
| 12 | 8 | 20 | 26 | 21 | 19 |
| 18 | 10 | 24 | 26 | 22 | 26 |
| 25 | 11 | 26 | 25 | 25 | 37 |

TABLE 4

TABLE 4: VARIATION OF APHA VALUE DEPENDING ON TEMPERATURE (WATER ADDITION AMOUNT: 50% BY WEIGHT)

| ELAPSED | PRESERVATION TEMPERATURE | | | | |
|---|---|---|---|---|---|
| DAYS | −20° C. | 5° C. | 20° C. | 40° C. | 60° C. |
| 0 | 5 | 5 | 5 | 5 | 5 |
| 2 | 4 | 5 | 3 | 10 | 6 |
| 12 | 4 | 6 | 3 | 6 | 18 |
| 18 | 5 | 8 | 3 | 8 | 37 |
| 25 | 6 | 8 | 4 | 9 | 67 |

Even when water is added or not added, it was confirmed that coloration tended to develop with an increase in temperature.

As shown in Table 4, it was confirmed that in the 1,5-PD solution having a water addition amount of 50% by weight, the development of coloration with an increase in temperature could be further suppressed as compared with the case of no addition of water, and coloration could be markedly prevented in preservation at lower than 60° C.

<4> Evaluation Test 1 of Stability Depending on Preservation Material Quality

Ultrapure water was added to 100% by weight 1,5-PD liquid prepared in the above <1> to prepare a 1,5-PD solution having a water addition amount of 8% by weight, that is a 92% by weight 1,5-PD solution as a test solution. The APHA value of the test solution was measured and found to be 17.

Various packing materials usable for a container and the like were cut if necessary to prepare 0.5 g of test packing materials. 0.5 g of test packing materials were each individually added to 30 mL of the test solution in a glass flask, and stirred for 5 days, and allowed to stand for 13 days. 18 Days after addition of the test packing materials, the test packing materials were visually observed and the APHA value of the 1,5-PD solution was measured. For the 18 days after addition of each of the test packing materials to the glass flask, the glass flask was placed under a temperature condition of 20° C. The results of measurement are shown in Table 5.

TABLE 5

TABLE 5: EVALUATION OF STABILITY DEPENDING ON PRESERVATION MATERIAL 1

| TEST PACKING MATERIAL | APHA | VISUAL OBSERVATION |
|---|---|---|
| NO ADDITION | 17 | |
| IRON | 16 | NO CHANGE |
| POLYPROPYLENE | 16 | NO CHANGE |
| HDPE | 17 | SLIGHTLY YELLOWED |
| LDPE | 170 | PROMINENTLY YELLOWED |
| SILICON | 37 | SLIGHTLY YELLOWED |
| RUBBER | 548 | PROMINENTLY YELLOWED, INCLUDING INSOLUBLE COMPONENT |
| POLYVINYLIDENE CHLORIDE | 999 | DARKENED IMMEDIATELY AFTER ADDITION, INCLUDING INSOLUBLE COMPONENT, NOT PHASE-SEPARATED |

<5> Evaluation Test 2 of Stability Depending on Preservation Material Quality

A test liquid and test packing materials were prepared in the same manner as in the above <3>. 0.5 g of the test packing materials were each individually added to 30 mL of the test liquid in a glass flask. The glass flask was placed in a water bath at 50° C., and the each test liquid was preserved with stirring. 9 Days after addition of each of the test packing materials, the test packing materials were visually observed and the APHA value of 1,5-PD solution was measured. The results are shown in Table 6.

TABLE 6

TABLE 6: EVALUATION OF STABILITY DEPENDING ON PRESERVATION MATERIAL 2

| TEST PACKING MATERIAL | APHA | VISUAL OBSERVATION |
|---|---|---|
| NO ADDITION | 17 | |
| IRON | 999 | PROMINENTLY BROWNISH-REDISH |
| POLYPROPYLENE | 44 | NO CHANGE |
| HDPE | 52 | SLIGHTLY YELLOWED |
| LDPE | 406 | PROMINENTLY YELLOWED |
| SILICON | 194 | SLIGHTLY YELLOWED |
| RUBBER | 999 | PROMINENTLY YELLOWED, INCLUDING INSOLUBLE COMPONENT |
| POLYVINYLIDENE CHLORIDE | 999 | DARKENED IMMEDIATELY AFTER ADDITION, INCLUDING INSOLUBLE COMPONENT, NOT PHASE-SEPARATED |

<6> Evaluation Test 3 of Stability Depending on Preservation Material Quality

100% by weight 1,5-PD liquid prepared in the above <1> was redistilled to prepare a test solution. A portion of the packing materials used in the above <4>, polytetrafluoroethylene (PEFE, trade name: TEFLON), and stainless steels (Japanese Industrial Standards, material mark: SUS304 and SUS316L) were prepared as test packing materials.

0.5 g of the test packing materials were each individually added to the test liquid in a glass flask, the glass flask was placed in a water bath adjusted to 20° C., and each test liquid was preserved with stirring for a predetermined period of time. The APHA value was measured at each predetermined time. The results are shown in Table 7.

TABLE 7

EVALUATION OF STABILITY DEPENDING ON PRESERVATION MATERIAL 3

| TEST PACKING MATERIAL | 0 DAY | 3 DAYS | 7 DAYS | 14 DAYS | 22 DAYS | 143 DAYS |
|---|---|---|---|---|---|---|
| NO ADDITION | 3 | 3 | 4 | 5 | 6 | 12 |
| IRON | 3 | 5 | 8 | 126 | 127 | 132 |
| POLYPROPYLENE | 3 | 4 | 4 | 4 | 4 | 7 |
| HDPE | 3 | 4 | 5 | 4 | 5 | 6 |
| LDPE | 3 | 15 | 19 | 24 | 28 | 64 |
| SILICON | 3 | 8 | 8 | 9 | 10 | 14 |
| PTFE | 4 | 4 | 4 | 4 | — | — |
| STAINLESS STEEL (SUS304) | 4 | 4 | 5 | 5 | — | — |
| STAINLESS STEEL (SUS316L) | 4 | 4 | 5 | 5 | — | — |

The present invention is useful in an industry using 1,5-PD or a salt thereof, for example, fields of resin, synthetic fiber, pharmaceutical, and the like.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for preserving purified 1,5-pentanediamine or a salt thereof which has a water content, the method comprising:
   adjusting said water content in the purified 1,5-pentanediamine or a salt thereof to more than 1% by weight and not more than 50% by weight.

2. The method according to claim 1, wherein said adjusting comprises adding water to the purified 1,5-pentanediamine or a salt thereof.

3. The method according to claim 2, wherein said adjusting comprises adding water so that said water content is 3% by weight or more and not more than 8% by weight; wherein said purified 1,5-pentanediamine or a salt thereof has a purity of 98% by weight or more.

4. The method according to claim 1, wherein said adjusting is performed at a temperature of 40° C. or lower.

5. The method according to claim 1, wherein said purified 1,5-pentanediamine or a salt thereof is not in contact with iron, a low density polyethylene, silicon, a rubber, and polyvinylidene chloride.

6. The method according to claim 1, wherein said adjusting is conducted in a container which includes an inner face that is in contact with said purified 1,5-pentanediamine or a salt thereof, and is coated with glass, polypropylene, a high density polyethylene, a stainless steel, or polytetrafluoroethylene.

7. A method for preventing discoloration of purified 1,5-pentanediamine or a salt thereof which has a water content, the method comprising:
   adjusting said water content in the purified 1,5-pentanediamine or a salt thereof to more than 1% by weight and not more than 50% by weight.

8. A packaged 1,5-pentanediamine or salt thereof, comprising:
   a container for preservation of 1,5-pentanediamine or a salt thereof; and purified 1,5-pentanediamine or a salt thereof contained in the container;

wherein the container includes an inner face in contact with the 1,5-pentanediamine or a salt thereof, said inner face is coated with glass, polypropylene, a high density polyethylene, a stainless steel, or polytetrafluoroethylene, and wherein iron, a low density polypropylene, silicon, a rubber, and polyvinylidene chloride are not exposed on said inner face;

wherein a water content in the 1,5-pentanediamine or a salt thereof is more than 1% by weight and not more than 50% by weight.

* * * * *